(12) United States Patent
Parker et al.

(10) Patent No.: US 9,901,576 B2
(45) Date of Patent: Feb. 27, 2018

(54) STABLE FORMULATION OF PHENOBARBITAL SODIUM INJECTION

(71) Applicant: WEST-WARD PHARMACEUTICALS INTERNATIONAL LIMITED, London (GB)

(72) Inventors: Michael G. Parker, Cherry Hill, NJ (US); Scott S. Wilson, Cherry Hill, NJ (US); Yasmeen Chahal, Cherry Hill, NJ (US); Kelly W. Hovius, Cherry Hill, NJ (US); David E. McAnany, Cherry Hill, NJ (US)

(73) Assignee: West-Ward Pharmaceuticals International Limited, London (GB)

( * ) Notice: Subject to any disclaimer, the term of this patent is extended or adjusted under 35 U.S.C. 154(b) by 0 days.

(21) Appl. No.: 15/355,868

(22) Filed: Nov. 18, 2016

(65) Prior Publication Data
US 2017/0143719 A1    May 25, 2017

Related U.S. Application Data

(60) Provisional application No. 62/258,000, filed on Nov. 20, 2015.

(51) Int. Cl.
| | |
|---|---|
| *A61K 31/515* | (2006.01) |
| *A61K 9/08* | (2006.01) |
| *A61K 9/00* | (2006.01) |
| *A61K 47/10* | (2017.01) |
| *B65B 7/16* | (2006.01) |
| *B65B 3/00* | (2006.01) |
| *B65B 55/02* | (2006.01) |
| *A61J 1/06* | (2006.01) |

(52) U.S. Cl.
CPC ............... *A61K 31/515* (2013.01); *A61J 1/06* (2013.01); *A61K 9/0019* (2013.01); *A61K 9/08* (2013.01); *A61K 47/10* (2013.01); *B65B 3/003* (2013.01); *B65B 7/16* (2013.01); *B65B 55/02* (2013.01)

(58) Field of Classification Search
CPC ...... A61K 31/515; A61K 9/08; A61K 9/0019; A61K 47/10
See application file for complete search history.

(56) References Cited

U.S. PATENT DOCUMENTS

| | | | |
|---|---|---|---|
| 1,984,733 A | 12/1934 | Forbing | |
| RE25,502 E | 12/1963 | de Beer | |
| 5,141,961 A | 8/1992 | Coapman | |
| 5,164,416 A | 11/1992 | Nagai et al. | |
| 5,958,946 A | 9/1999 | Styczynski et al. | |
| 5,965,603 A | 10/1999 | Johnson et al. | |
| 6,627,211 B1 | 9/2003 | Choi et al. | |
| 7,335,379 B2 | 2/2008 | Carrara et al. | |
| 8,187,615 B2 | 5/2012 | Friedman | |
| 9,517,269 B1* | 12/2016 | Brynjelsen | ............ A61K 47/10 |
| 2002/0010164 A1* | 1/2002 | Abrahamson | ............ A61K 9/08 514/167 |
| 2006/0153905 A1 | 7/2006 | Carrara et al. | |
| 2010/0035904 A1 | 2/2010 | Sun et al. | |
| 2012/0129799 A1 | 5/2012 | Mukesh et al. | |
| 2013/0210729 A1 | 8/2013 | So et al. | |

FOREIGN PATENT DOCUMENTS

| | | |
|---|---|---|
| RU | 2 463 052 C1 | 10/2012 |
| WO | 02/056878 A2 | 7/2002 |
| WO | 2006/125774 A1 | 11/2006 |

OTHER PUBLICATIONS

Manage Markets (https://client.formularynavigator.com/Search.aspx?siteTestID=1537&targetScreen=4&drugBrandListBaseKey=butalbital-aspirin-caffeine+50+mg–325+mg–40+mg+tablet) 2013.*

Gupta, "Effect of ethanol, glycerol, and propylene glycol on the stability of phenobarbital sodium," Journal of Pharmaceutical Sciences, 73(11):1661-1662 (Nov. 1984). Abstract. http://onlinelibrary.wiley.com/doi/10.1002/jps.2600731149/abstract (downloaded from the on Internet Jun. 23, 2015).

Kapadia et al., "Separation of decomposed products of phenobarbital sodium by paper chromatographic technique," Journal of the American Pharmaceutical Association, 48(7):407-409 (Jul. 1959). Abstract. http://onlinelibrary.wiley.com/doi/10.1002/jps.3030480712/abstract (downloaded from the Internet on Jun. 23, 2015).

Williams et al., "Excess free energy approach to the estimation of solubility in mixed solvent systems III: Ethanol-propylene glycol-water mixtures," Journal of Pharmaceutical Sciences, 73(1):18-23 (Jan. 1984). Abstract. http://onlinelibrary.wiley.com/doi/10.1002/jps.2600730106/abstract (downloaded from the Internet on Jun. 23, 2015).

(Continued)

*Primary Examiner* — Shirley V Gembeh
(74) *Attorney, Agent, or Firm* — Winston & Strawn LLP

(57) ABSTRACT

Stable phenobarbital sodium solutions for injection that do not generate impurities during extended storage. These solutions include phenobarbital sodium in an amount of 15 to 200 mg/mL; a C1-C4 alcohol such as ethanol in an amount of 105 to 160 mg/mL; and a glycol such as propylene glycol in an amount of between 620 and 830 mg/mL and have a pH of between 9 and 12 which is adjusted to that range by adding acid or base, as required. No more than 50 mg/mL water is present including any water introduced by the acid or base. The solutions contain no more than 0.8% of phenyl ethyl acetyl urea impurity as well as no detectable amount of phenyl butyric acid after two years storage at room temperature.

17 Claims, No Drawings

(56) References Cited

OTHER PUBLICATIONS

International Search Report and Written Opinion, Appl. No. PCT/IB2016/056973, dated Jan. 27, 2017.
Torrellas et al., "Pituitary-Adrenal Responses to Sub-Chronic Treatment with Phenobarbital and/or Phenytoin (Diphenylhydantoin) in Rats," Pharmacology Biochemistry & Behavior, 15:235-241 (1981).

* cited by examiner

STABLE FORMULATION OF PHENOBARBITAL SODIUM INJECTION

This application claims the benefit of U.S. provisional application No. 62/258,000 filed Nov. 20, 2015, the entire content of which is expressly incorporated herein by reference thereto.

BACKGROUND

The present invention relates to a phenobarbital sodium solution formulation that is more stable under various stress conditions then prior art formulations and that includes a reduced impurity profile and faster dissolution rate.

A number of phenobarbital injection USP products are currently available on the US and international markets for various treatments, including as a medication for partial and generalized tonic-clonic seizures as well as for treatment of neonatal seizures. The injectable form is primarily used to control status epilepticus.

To prepare phenobarbital sodium formulations for injection, the compound is typically dissolved in a solvent. While the compound is freely soluble in water with solubility reported to be as high as 333 mg/mL to 1 g/mL), the presence of hydroxyl ions in the formulation from the water results in a hydrolysis pathway that can destroy the phenobarbital ring complex. This destruction results in the possible formation of impurities including harmful degradants or precipitates. Furthermore, some of the impurities do not possess a chromophore and therefore are not capable of detection by standard UV-Vis detectors with HPLC analytical methodology. Thus, it is desired to minimize or preferably eliminate any impurities in commercial phenobarbital sodium injection formulations.

The solution to the problem then easily becomes removal of water from the formulation. This is easier said than done as it is highly difficult to dissolve phenobarbital sodium in any organic solvent alone, even when utilizing an aggressive turbulent flow for mixing the active and solvent together. Instead, the prior art generally suggests that a common method for minimizing phenobarbital degradation in solution dosage forms is to dissolve the drug in a mixed solvent of water with organic solvents such as alcohol, sorbitol, propylene glycol, glycerol, polyethylene glycol, and others. This assumes and requires the inclusion of some water for dissolution purposes. As phenobarbital sodium is not as soluble in solvents such as, e.g., ethanol, with solubility reported to only be as high as 100 mg/mL, some water is typically included in formulations that include ethanol or other liquids as primary solvents. The water content, in general, is on the order of 8 to 12% by weight or more of such solvent mixtures.

The typical impurities for phenobarbital solutions that include water as part of the solvent system are phenyl ethyl acetyl urea (PEAU) and phenyl butyric acid (PBA). Currently, the limits for such impurities in commercially marketed pharmaceutical products are up to 10% of PEAU and up to 1.0% of PBA. The impurities are measured after storage of the solution at room temperature for 2 years. As an accelerated test, the impurities are measured after storage of the solution at a temperature of 40° C. for three months. Room temperature is defined as "near 25° C." and is typically understood as being between the ordinary temperatures of approximately 18.3° C. to 26.7° C. of the atmosphere in a laboratory.

Other possible degradation products of phenobarbital sodium can result from other conditions, such as reactions with base, oxidation or subjecting the compound to heat. These degradation products are illustrated in Table 1 below:

TABLE 1

Degradation Products of Phenobarbital Sodium

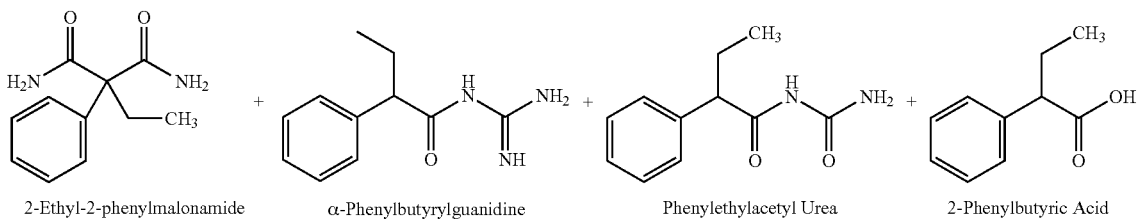

2-Ethyl-2-phenylmalonamide    α-Phenylbutyrylguanidine    Phenylethylacetyl Urea    2-Phenylbutyric Acid

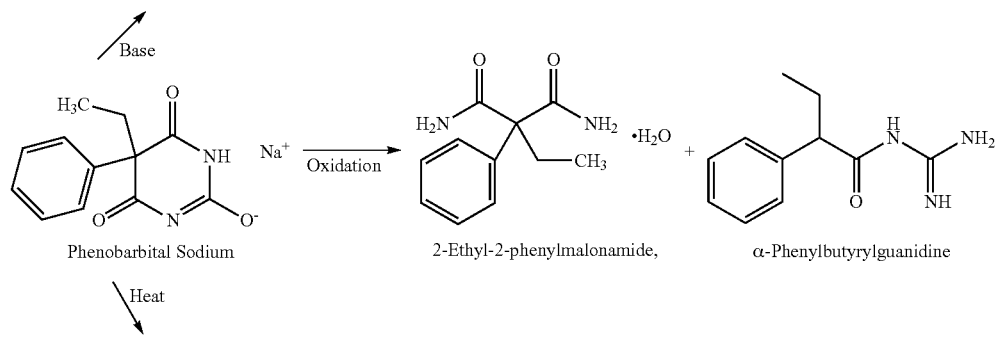

Phenobarbital Sodium    2-Ethyl-2-phenylmalonamide,    α-Phenylbutyrylguanidine

TABLE 1-continued

Degradation Products of Phenobarbital Sodium

| 2-Ethyl-2-phenylmalonamide | Phenylethylacetyl Urea | 2-Phenylbutyric Acid |

The following prior art documents are cited as particular examples of solvent mixtures that have been used for phenobarbital sodium solutions or for other pharmaceuticals that cannot be solubilized in water.

U.S. Pat. No. 6,627,211, which discloses a solvent mixture for transmucosal delivery of an anticonvulsant agent, such as a diazepam, wherein the solvent mixture comprises, e.g., 30% of a C1-C5 aliphatic alcohol such as ethanol, 60% of a glycol such as propylene glycol and 10% water along with a biological surfactant of a bile salt or lecithin to assist in the transmucosal permeation of the anticonvulsant agent.

U.S. Pat. No. 5,141,961, which discloses a process for solubilizing various pharmaceuticals that are difficult to solubilize in water. These pharmaceuticals are solubilized in a mixture of a polyethylene glycol and a polyvinylpyrrolidone. A typical formulation includes 20% to 70% of propylene glycol along with 1 to 28% of a polyvinylpyrrolidone and a water content that is 8% or less. A solvent of a C1-C4 aliphatic alcohol, typically ethanol, can be used in an amount of 1 to 50% to prepare mixtures of the ingredients but thereafter is evaporated from the formulation.

US patent publication 2006/0153905 discloses transdermal or transmucosal pharmaceutical formulations that include at least one pharmacologically active ingredient, and a solvent system having a monoalkylether of diethylene glycol and a glycol present in specified ratios, and a mixture of water and alcohol. The document discloses the use of 6% propylene glycol and 47% ethanol with water and other components.

PCT publication WO 2006/125774 discloses an oral formulation of topiramate that has a low water content to prevent hydrolysis of the active and to extend the storage life of the formulation. The water content of such formulations is no more than 5%. The solvents that are used include ethanol, propylene glycol, or polyethylene glycols, alone or in various combinations. These solutions also contain various preservatives and antioxidants in order to form stable solutions at pH values of 5 to 8.

An article by Gupta, V. D., Effect of ethanol, glycerol and propylene glycol on the stability of Phenobarbital Sodium, J. Pharm. Sci., 1984, 73:1661-2, reports on the effects that these solvents have on the stability of phenobarbital solutions. For stabilization, Gupta discloses that ethanol had the best effect followed by propylene glycol and glycerol compared to the stability of phenobarbital in water alone. The preferred solutions included 20% of ethanol, propylene glycol or glycerol in water. As noted herein, however, such a large amount of water is not desirable from the standpoint that it will likely cause hydrolysis of the phenobarbital ring and the generation of undesirable impurities.

A number of other prior art documents disclose the stability of phenobarbital in various aqueous solutions that can contain propylene glycol, ethanol, or other solvents. As noted, however, such aqueous solutions are not desirable in pharmaceutical products due to the generation of impurities over time.

An article by Williams, N. A. et al., "Excess free energy approach to the estimation of solubility in mixed solvent systems III: Ethanol-propylene glycol-water mixtures," J. Pharm Sci (January, 1984), 73(1): 18-23, describes the applicability of the Wohl excess free energy expression to describe the solubility of phenobarbital in various mixtures including ethanol or propylene glycol combined together or with water. Williams concludes that the equation does not satisfactorily describe solubility for phenobarbital in ethanol/propylene glycol solutions even though solubility is fairly high because the assumptions made in the derivation of the equation do not hold, but that the equation is acceptable for describing the solubility of solutions that contain water.

As noted, the inclusion of significant amounts of water in phenobarbital sodium formulations is not desirable as it will likely result in the formation of undesirable amounts of impurities. Thus, there is a need for formulations that contain or generate relatively low amounts of such impurities. The present invention now addresses the need for stable, essentially impurity-free formulations.

SUMMARY OF THE INVENTION

The present invention now provides, for the first time, phenobarbital solutions for injection that are extremely stable and that do not generate any significant amounts of impurities during extended storage. Generally, these phenobarbital solutions include a phenobarbital salt, preferably phenobarbital sodium, in an amount of 15 to 200 mg/mL and in particular 25 to 150 mg/mL; a C1-C4 alcohol, preferably ethanol, in an amount of 105 to 160 mg/mL and in particular 125 to 150 mg/mL; and a glycol such as propylene glycol in an amount of between 620 and 830 mg/mL and in particular 675 to 810 mg/mL. Advantageously, these solutions have a pH of between 9 and 12 and in particular between 9.2 and 10.2 which is adjusted to that range by adding a sufficient amount of acid or base, as required. These solutions contain no more than 50 mg/mL water including any water introduced by the acid or base that is added to provide the desired pH. The enhanced stability of these solutions is demonstrated by the fact that they contain no more than 0.8% of PEAU impurity after two years storage at room temperature. Furthermore, these solutions do not contain a detectable amount of PBA impurity after the same periods of two years storage at room temperature.

The present invention provides a substantial reduction of impurities due to the greatly enhanced stability of such solutions compared to conventional or currently available commercial solutions of phenobarbital sodium for injection.

This reduction of impurities is based on the careful selection and balance of the solvent systems disclosed herein.

DETAILED DESCRIPTION OF THE INVENTION

In the following detailed description, numerous specific details are set forth by way of examples in order to provide a thorough understanding of the relevant teachings. It should be apparent to those skilled in the art, however, that the present teachings may be practiced without such details. In other instances, well known methods, procedures and/or formulation details have been described at a relatively high-level, without detail, in order to avoid unnecessarily obscuring aspects of the present teachings.

The invention may be more fully understood by reference to the following definitions.

When the singular forms "a," "an" and "the" or like terms are used herein, they will be understood to include plural referents unless the context clearly dictates otherwise. Thus, for example, reference to "a pharmaceutical carrier" includes mixtures of two or more such carriers, and the like. The word "or" and like terms mean any one member of a particular list and also includes any combination of members of that list.

When used herein the term "about" will compensate for variability allowed for in the pharmaceutical industry and inherent in pharmaceutical products, such as differences in product strength and bioavailability due to manufacturing variations and time-induced product degradation. The term allows for any variation which in the practice of pharmaceuticals would allow the product being evaluated to be considered pharmaceutically equivalent or bioequivalent, or both if the context requires, to the recited strength of a claimed product. Alternatively, the term can allow for up to 5, 10, 15 or 20% variation from the stated value. Where particular values are described in the application and claims, unless otherwise stated, the term "about" is implicit and in this context means within an acceptable error range for the particular value.

Throughout the description and claims of this specification, the word "comprise" and variations of the word, such as "comprising" and "comprises," means "including but not limited to," and is not intended to exclude, for example, other additives, components, integers or steps. The term "consisting essentially of" means that other additives or components that impart a material change to the invention are not encompassed by the claims. For example, a stable formulation consisting essentially of recited components would exclude other additives that are conventionally used for imparting stability or anti-oxidant properties to the formulation, as these additives are not needed based on the components that are specifically recited to be present.

When ranges are given by specifying the lower end of a range separately from the upper end of the range, it will be understood that the range can be defined by selectively combining any one of the lower end variables with any one of the upper end variables that is mathematically possible. Also, when reciting ranges between certain values, the endpoints are considered to be included in the recited range.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts that are pharmaceutically acceptable, as defined above, and that possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when an acidic proton present is capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. The preferred phenobarbital salt is phenobarbital sodium.

The term "pharmaceutical solution" or "solution" refers to a mixture with a pharmaceutically suitable excipient, diluent or carrier selected with regard to the intended route of administration and standard pharmaceutical practice. The excipient, diluent and/or carrier must be "acceptable" in the sense of being compatible with the other ingredients of the solution and not deleterious to the recipient thereof. Acceptable excipients, diluents, and carriers for therapeutic use are well known in the pharmaceutical art, and are described, for example, in Remington: The Science and Practice of Pharmacy, Lippincott Williams & Wilkins (A. R. Gennaro edit. 2005). The choice of pharmaceutical excipient, diluent, and carrier can be selected with regard to the intended route of administration and standard pharmaceutical practice. The most preferred excipients, diluents and carriers are disclosed herein and in the examples.

The present formulations are designated as "stable" if they provide the same or less total impurities when exposed to a wider range of system parameters, i.e., oxygen head space, pH, and temperature. In particular, the stable formulations of the present invention have been found to exhibit 1% or less, preferably 0.8% or less of hydrolysis impurities.

As a skilled artisan would know, "hydrolysis impurities" refers to impurities that result from hydrolysis of the phenobarbital ring as precipitates or other degradation products. The typical impurities for phenobarbital solutions are PEAU and PBA. As noted herein, current limits for such impurities in commercial products are up to 10% of PEAU and up to 1% of PBA. The impurities are measured after storage of the solution at room temperature for 2 years.

As noted herein, the phenobarbital solutions of the invention include the phenobarbital salt, phenobarbital sodium. This is a well-known and conventionally used active which is established for various treatments. The general amount of this compound to be included in solutions for injection is from about 15 to about 200 mg/mL, including the endpoints although any other amount in the recited ranges should be suitable. The upper end of the range is a maximum concentration that does not precipitate in the particular formulation, while on the lower end, the minimum amount to be used would be one that provides a pharmacological effect without requiring repeated injections of lower concentrations to achieve such an effect. More specifically, the amount may be between 30 and 135 mg/mL and in particular between 40 and 130 mg/mL, with the most preferred amounts being between formulations that contain 30, 55, 65, 90 or 130 mg/mL.

The solvent mixture comprises two major components, namely an alcohol and a glycol. The alcohol is preferably a C1-C4 alcohol, and preferably is an aliphatic alcohol. The most preferred alcohol is ethanol, as it is well understood by skilled artisans and has been commonly used in many different formulations in the art. The amount of alcohol may be between about 125 to about 160 mg/mL. Preferably, the amount should be between 135 and 150 mg/mL with a target amount of about 140 mg/mL.

The glycol is preferably propylene glycol, which is another solvent that is well understood by skilled artisans and commonly used in many different formulations in the art. The amount of the glycol may be between about 620 and 830 mg/mL. Preferably, the amount is between 700 and 810 mg/mL with the most preferred amounts being determined by routine testing of the formulation provided that it is in the general range described herein. Often, the amount is between 725 and 785 mg/mL and the most preferred amount is between about 750 and about 760 mg/mL.

Advantageously, these solutions have a pH of between 9 and 12, and preferably from 9.2 to 10.2, with the pH of the solution adjusted to that range by adding a sufficient amount of acid or base, as required. While any acid or base can be used for this purpose, it has been found that hydrochloric acid and sodium hydroxide are eminently suitable and are preferred due to their well-known nature.

In contrast to the prior art, the phenobarbital sodium solutions of the present invention provide a substantial reduction of PEAU and PBA impurities. To assist in maintaining the impurities at such low levels, the solutions of the invention contains no more than 50 mg/mL water and preferably 40 mg/mL or less including the water that is introduced by the acid or base that is added to provide the desired pH. The enhanced stability of these solutions is demonstrated by the fact that the solution contains no more than 0.8% of PEAU impurity after two years storage at room temperature. Furthermore, these solutions do not contain a detectable amount of PBA after the same period.

The preferred concentrations of phenobarbital sodium range from 30 to 135 mg/mL. These amounts can be effectively and easily dissolved in the preferred 50-50 mixture of ethanol and propylene glycol to form a stable solution containing very small amounts of water. This reduction in water content leads to the prevention or significant reduction of impurities as the amount of water is insufficient to cause any significant hydrolysis of the phenobarbital ring. As noted, the amount of PEAU impurity is at least about 8 to 9 times lower than that which is currently allowed in commercial products while any amount of PBA is effectively eliminated from these solutions. Also, the reduced amount of impurity formation in the pH range of 9 to 12 and preferably from 9.2 to 10.2 would reduce the propensity for loss of mass balance in an analytical test method utilizing a UV-Vis detector.

These compositions do not need to contain and are typically free from including any preservatives, anti-oxidants, wetting agents, emulsifying agents, surfactants or dispersing agents. If desired, such components can be added in conventional amounts but it is preferred that they not be present. The same is true of other additives for the prevention of the action of microorganisms: there is no need for the inclusion of various antibacterial and antifungal agents, for example, paraben, chlorobutanol, phenol sorbic acid, and the like, but they can be added if desired.

Additionally, it is preferred that the solution not contain any other drug active. This assists in avoiding impurities. In more preferred embodiments, the solutions consist essentially of or even consist of the recited components.

And while the present formulations are described in terms of concentrations of the various components, the formulations are distinct from the prior art even when the relative percentages of the components is considered. Converting the concentrations of the ingredients to percentages, it is seen that the present invention utilizes a solvent solution that is between about 40 and about 60% of ethanol and about 60 to about 40% of propylene glycol for dissolution of the phenobarbital sodium API. Preferably, equal amounts of each solvent are used. While the solvent solution does contain a small amount of water, in an amount of 5.0% or less and preferably 3.5% or less, water is not intentionally added to the solvent solution. It is instead introduced from the addition of the acid or base used to adjust the pH of the solution to the preferred value of 9.2 to 10.2.

Accordingly, the preferred formulations of the invention are those wherein:

(a) the phenobarbital sodium is present in an amount of 25 mg/mL;
the C1-C4 alcohol is ethanol and is present in an amount of about 140 mg/mL;
the polypropylene glycol is present in an amount of about 809 mg/mL; and
wherein the solution contains no more than 40 mg/mL water;

(b) the phenobarbital sodium is present in an amount of 55 mg/mL;
the C1-C4 alcohol is ethanol and is present in an amount of about 140 mg/mL;
the polypropylene glycol is present in an amount of between 779 mg/mL; and
wherein the solution contains no more than 40 mg/mL water;

(c) the phenobarbital sodium is present in an amount of 90 mg/mL;
the C1-C4 alcohol is ethanol and is present in an amount of about 140 mg/mL;
the polypropylene glycol is present in an amount of about 754 mg/mL; and
wherein the solution contains no more than 40 mg/mL water;

(d) the phenobarbital sodium is present in an amount of 150 mg/mL; and
the C1-C4 alcohol is ethanol and is present in an amount of about 140 mg/mL;
the polypropylene glycol is present in an amount of about 694 mg/mL; and
wherein the solution contains no more than 40 mg/mL water.

Other concentrations of the phenobarbital sodium, such as 30, 65 or 130 mg/mL can be used. In all of the foregoing formulations, the preferred C1-C4 alcohol is ethanol and is present in an amount of between about 120 and 160 mg/mL, the polypropylene glycol is present in an amount of about 620 to 830 mg/mL; and the water is typically present at about 36 mg/mL or less.

Another embodiment of the invention relates to a method of making an injection solution of phenobarbital sodium by admixing from solvents together with the active agent and then adjusting the pH to the desired range as necessary. The method then calls for filling an appropriate container, such as a pre-filled syringe, vial, or the like, with about 0.5 to about 20 mL of the solution. After admixing the components solutions and filling the appropriate container, the product is subject to sterilizing and the container is sealed. The invention calls for providing a headspace in the sealed container consisting of less than 10% by volume of oxygen content and preferably below 5% by volume by adding nitrogen to the container. As noted, this is achieved by adding nitrogen to the container during filling with the solution.

EXAMPLES

The present invention is now further identified and defined by the following examples, which illustrate the most preferred embodiments.

Example 1: Comparison of Phenobarbital Sodium Injection Formulations of the Present Invention and Prior Art Marketed Formulations

TABLE 2

| | | Formulations | | | | |
|---|---|---|---|---|---|---|
| Purpose | Raw Material | Currently Marketed Formulations | Inventive Formulations | | | |
| Active | Phenobarbital Sodium, USP | 65 mg/mL and 130 mg/mL | 25 mg/mL | 55 mg/mL | 90 mg/mL | 150 mg/mL |
| Co-Solvent | Ethanol, Dehydrated, USP | 105.5 mg/mL | 140 mg/mL | 140 mg/mL | 140 mg/mL | 140 mg/mL |
| Co-Solvent | Propylene Glycol, USP$^A$ | 702.4 mg/mL | QS to 100% Approx. 809 mg/mL | QS to 100% Approx. 779 mg/mL | Q.S. to 100% Approx. 754 mg/mL | QS to 100% Approx. 694 mg/mL |
| Preservative | Benzyl Alcohol | 15.63 mg/mL | N/A | N/A | N/A | N/A |
| pH Adjuster | 1:5 Hydrochloric Acid, NF | As required to adjust pH | As required to adjust pH | As required to adjust pH | As required to adjust pH | As required to adjust pH |
| | 1:10 Sodium Hydroxide, NF | As required to adjust pH | As required to adjust pH | As required to adjust pH | As required to adjust pH | As required to adjust pH |
| Diluent | Water for Injection$^B$, USP | QS to 100% About 8% to 12% w/w | 36 mg/mL 3.53%$^C$ | 36 mg/mL 3.53%$^C$ | 36 mg/mL 3.53%$^C$ | 36 mg/mL 3.53%$^C$ |

$^A$The amount of Propylene Glycol addition is based on a calculation utilizing the density.
$^B$The water for injection (WFI) amount is as follows: Propylene Glycol [mg/mL] = Density [mg/mL] − summation of all other ingredients [mg/mL]. Batch record will read "Q.S. to final batch weight".
$^C$WFI concentration is listed with the inclusion of water (acid) added by pH adjustment.

In general, the solutions of the present invention contain much less water than prior art formulations and do not need to include a preservative. Basically, the relative amount of propylene glycol would be between 66 and 82%, the amount of ethanol would be between 10 and 16% and the amount of water would be less than 5% and preferably 3.5% or less. These values do not always add up to 100% due to the miscibility of the components in each other.

Tables 3 and 4 below illustrate the properties and performance of prior art formulations, one of which contains 65 mg/mL phenobarbital sodium and the other of which contains 130 mg/mL. Both tables show the water content, pH and assay percentage for those formulations, while Table 3 shows accelerated degradation data at 40° C. for the 65 mg/mL solution and Table 4 shows accelerated degradation data at 40° C. for the 130 mg/mL solution. Various headspace oxygen contents were used, typically at 21% (atmospheric content) or at 5% (reduced content due to nitrogen flushing of the container during filling).

TABLE 3

Prior Art 65 mg/mL (11.6% Water) Accelerated Degradation at 40° C. Data

| Sample ID | Storage Temp ° C. | Oxygen High/Low | Duration (Month) | Assay | pH | 2-Phenylburtyric Acid (PBA) % | Phenylethylacetyl Urea (PEAU) % | Total % Impurities |
|---|---|---|---|---|---|---|---|---|
| PB3-7  | 25 | 21% | 0 | 95.4 | 9.4 | ND   | 0.05 | 0.1  |
| PB3-19 | 40 | 21% | 1 | 92.2 | 9.4 | ND   | 2.00 | 2.0  |
| PB3-20 | 40 | 21% | 2 | 88.9 | 9.4 | 0.20 | 4.80 | 5.0  |
| PB3-21 | 40 | 21% | 3 | 86.0 | 9.4 | 0.38 | 5.52 | 5.9  |
| PB3-13 | 25 | 5%  | 0 | 94.3 | 9.5 | ND   | 0.05 | 0.1  |
| PB3-23 | 40 | 5%  | 1 | 92.8 | 9.4 | ND   | 1.90 | 1.9  |
| PB3-24 | 40 | 5%  | 2 | 91.0 | 9.4 | 0.10 | 4.20 | 4.3  |
| PB3-25 | 40 | 5%  | 3 | 78.8 | 9.4 | 1.81 | 9.12 | 10.9 |

TABLE 4

Prior Art 130 mg/mL (8% Water) Accelerated Degradation at 40° C. Data

| Sample ID | Storage Temp ° C. | Oxygen High/Low | Duration (Months) | Assay | pH | PBA % | PEAU % | Total % |
|---|---|---|---|---|---|---|---|---|
| PB3-41 | 25 | 21% | 0 | 96.6 | 9.8 | ND | ND   | ND  |
| PB3-53 | 40 | 21% | 1 | 94.5 | 9.6 | ND | 0.60 | 0.6 |
| PB3-54 | 40 | 21% | 2 | 94.2 | 9.6 | ND | 1.13 | 1.1 |
| PB3-55 | 40 | 21% | 3 | 91.9 | 9.6 | ND | 1.77 | 1.8 |
| PB3-47 | 25 | 5%  | 0 | 98.7 | 9.6 | ND | ND   | ND  |
| PB3-57 | 40 | 5%  | 1 | 97.4 | 9.5 | ND | 0.70 | 0.7 |
| PB3-58 | 40 | 5%  | 2 | 95.4 | 9.5 | ND | 1.23 | 1.2 |
| PB3-59 | 40 | 5%  | 3 | 96.5 | 9.6 | ND | 1.78 | 1.8 |

The results in Table 3 shows an impurity level for the 65 mg/mL solution of 5.5% PEAU and 0.4% PBA for a total impurity level of 5.9% after three months storage at 40° C. in a container having 21% oxygen in the headspace, and an impurity level of 9.1% PEAU and 1.8% PBA for a total impurity level of 10.9% after three months storage at 40° C. in a container having 5% oxygen in the headspace. Similarly, the results for the 130 mg/mL solution in Table 4 show an impurity level of 1.8% PEAU and no detectable PBA for a total impurity level of 1.8% after three months storage at 40° C. in a container having 21% oxygen in the headspace, and the same values three months storage at 40° C. in a container having 5% oxygen in the headspace. The results are worse for the 65 mg/mL formulation because it contained 11.6% water while the 130 mg/mL formulation contained only 8% water.

Tables 5 to 7 illustrate test results for a solution of 55 mg/mL phenobarbital sodium solution according to the invention that contains only 3.5% water.

TABLE 5

90 mg/mL formulation (3.5% water) 3 Month 40° C. Data (pH of 10.2)

| Test ID # | Oxygen | Temp | Month | pH | Other Imp | PEMA | PEAU | PBA | Total |
|---|---|---|---|---|---|---|---|---|---|
| PB13-23 | 21% | 40° C. | 3 | 10.2 | 0.05 | <LOQ | 0.77 | 0.07 | 0.9% |
| PB13-27 | <5% | 40° C. | 3 | 10.2 | <LOQ | ND   | 0.63 | ND   | 0.6% |

Formulation also contains 140 mg/mL ethanol and 754 mg/mL propylene glycol.

TABLE 6

90 mg/mL formulation (3.5% water) 3 Month 40° C. Data (pH of 9.85)

| Test ID # | Oxygen | Temp | Month | pH | Other Imp | PEMA | PEAU | PBA | Total |
|---|---|---|---|---|---|---|---|---|---|
| PB13-67 | 21% | 40° C. | 3 | 9.85 | <LOQ | ND   | 0.79 | ND | 0.8% |
| PB13-71 | <5% | 40° C. | 3 | 9.85 | 0.05 | ND   | 0.71 | ND | 0.8% |

Formulation also contains 140 mg/mL ethanol and 754 mg/mL propylene glycol.

TABLE 7

90 mg/mL formulation (3.5% water) 3 Month 40° C. Data (pH of 9.5)

| Test ID # | Oxygen | Temp | Month | Other Imp | PEMA | PEAU | PBA | Total |
|---|---|---|---|---|---|---|---|---|
| PB13-111 | 21% | 40° C. | 3 | ND | ND | 0.82 | ND | 0.8% |
| PB13-115 | <5% | 40° C. | 3 | ND | ND | 0.74 | ND | 0.7% |

Formulation also contains 140 mg/mL ethanol and 754 mg/mL propylene glycol.

The results show significantly reduced impurity levels. In Table 5, the formulation that was exposed to atmospheric oxygen (21%) exhibited only 0.77% of PEAU and 0.07% of PBA impurities. For the same solution in a low oxygen environment, the impurity levels were reduced to 0.63 for PEAU and PBA was not even detected. Thus, these two products provided total impurity levels of 0.9 and 0.6% respectively.

Table 6 shows similar excellent results. The formulation that was exposed to atmospheric oxygen (21%) exhibited only 0.79% of PEAU and PBA was not detected. For the same solution in a low oxygen environment (5%), the impurity levels were reduced to 0.71 for PEAU and PBA was again not even detected. Thus, these two products each provided a total impurity level of 0.8%.

In Table 7, the formulation that was exposed to atmospheric oxygen (21%) exhibited only 0.82% of PEAU, while the same solution in a low oxygen environment exhibited 0.74% of PEAU. PBA was not even detected for either formulation. Thus, these two products provided total impurity levels of 0.8 and 0.7% respectively.

The results for each formulation in Tables 5 to 7 are more than 10 times lower than the maximum amount allowable for commercial products of phenobarbital solutions. These unexpected and significant improvements in impurity levels are obtained due to the 50/50 Ethanol/PEG dissolution solution and the reduced amount of water added only as a pH adjustment after an almost complete PEG to final volume. In Table 8 and 9, the results of three batches each of the preferred 55 mg/mL and 90 mg/mL invention, respectively, are shown to demonstrate the decrease in impurities under normal conditions. The results of these studies showed no detectable amounts of PBA were formed and the PEAU controlled to 0.7%.

TABLE 8

Preferred 55 mg/mL Formulation (3.5% Water) Stability Data at 25° C. Storage

| Batch | Duration (Month) | Assay | 2-Phenylburtyric Acid (PBA) % | Phenylethylacetyl Urea (PEAU) % | Total % Impurities |
|---|---|---|---|---|---|
| A | 0 | 99.9% | ND | ND | <LOQ |
| A | 6 | 100.3% | ND | 0.19% | 0.2% |
| A | 12 | 100.1% | ND | 0.37% | 0.4% |
| A | 24 | 100.7% | ND | 0.68% | 0.7% |
| B | 0 | 100.5% | ND | ND | <LOQ |
| B | 6 | 100.5% | ND | 0.20% | 0.2% |
| B | 12 | 100.7% | ND | 0.38% | 0.4% |
| B | 24 | 100.9% | ND | 0.69% | 0.7% |
| C | 0 | 99.9% | ND | ND | <LOQ |
| C | 6 | 101.7% | ND | 0.20% | 0.2% |
| C | 12 | 100.5% | ND | 0.37% | 0.4% |
| C | 24 | 100.9% | ND | 0.66% | 0.7% |

Formulation also contains 140 mg/mL ethanol and 779 mg/mL propylene glycol.

TABLE 9

Preferred 90 mg/mL Formulation (3.5% Water) Stability Data at 25° C. Storage

| Batch | Duration (Month) | Assay | 2-Phenylburtyric Acid (PBA) % | Phenylethylacetyl Urea (PEAU) % | Total % Impurities |
|---|---|---|---|---|---|
| A | 0 | 100.7% | ND | ND | <LOQ |
| A | 6 | 100.8% | ND | 0.21% | 0.2% |
| A | 12 | 100.5% | ND | 0.38% | 0.4% |
| A | 24 | 101.5% | ND | 0.69% | 0.7% |
| B | 0 | 99.8% | ND | ND | <LOQ |
| B | 6 | 100.9% | ND | 0.20% | 0.2% |
| B | 12 | 100.4% | ND | 0.36% | 0.4% |
| B | 24 | 100.0% | ND | 0.65% | 0.7% |
| C | 0 | 99.1% | ND | ND | <LOQ |
| C | 6 | 100.3% | ND | 0.22% | 0.2% |
| C | 12 | 99.4% | ND | 0.39% | 0.4% |
| C | 24 | 100.2% | ND | 0.70% | 0.7% |

Formulation also contains 140 mg/mL ethanol and 754 mg/mL propylene glycol.

All patents, patent applications, publications, test methods, protocols, literature, and other materials cited herein are hereby incorporated by reference in their entireties.

Those skilled in the art will appreciate that the present invention has a wide range of applications and that it fulfills the needs of the prior art described herein and meets the above-stated objects. While there has been shown and described preferred embodiments of the invention, it will be evident to those skilled in the art that various modifications and changes may be made thereto without departing from the spirit and the scope of the invention as set forth in the appended claims and equivalents thereof.

What is claimed is:

1. A phenobarbital sodium solution for injection comprising:
   phenobarbital sodium in an amount of 15 to 200 mg/mL;
   a C1-C4 alcohol in an amount of 105 to 160 mg/mL; and
   propylene glycol in an amount of between 620 and 830 mg/mL;
   wherein the solution has a pH of between 9 and 12 which is adjusted to that range by adding a sufficient amount of acid or base, as required;
   wherein the solution contains no more than 50 mg/mL water including any water introduced by the acid or base that is added to provide the desired pH; and
   wherein the solution contains no more than 0.8% of phenyl ethyl acetyl urea (PEAU) impurity after two years storage at room temperature.

2. The solution of claim 1, wherein:
   the phenobarbital sodium is present in an amount of 25 to 150 mg/mL;
   the C1-C4 alcohol is present in an amount of 125 to 150 mg/mL; and
   the propylene glycol is present in an amount of between 675 and 830 mg/mL; and
   the solution has a pH of between 9.1 and 10.2.

3. The solution of claim 1, wherein:
the phenobarbital sodium is present in an amount of 25 to 90 mg/mL;
the C1-C4 alcohol is ethanol and is present in an amount of about 140 mg/mL; and
the polypropylene glycol is present in an amount of between 730 and 830 mg/mL;
wherein the solution contains no more than 40 mg/mL water.

4. The solution of claim 1, wherein:
the phenobarbital sodium is present in an amount of 90 to 150 mg/mL;
the C1-C4 alcohol is ethanol and is present in an amount of about 140 mg/mL; and
the polypropylene glycol is present in an amount of between 660 and 785 mg/mL;
wherein the solution contains no more than 40 mg/mL water.

5. The solution of claim 1 which is free of preservatives or antioxidants.

6. The solution of claim 1 which does not contain a detectable amount of phenyl butyric acid (PBA) after two years storage at room temperature.

7. The solution of claim 1 which does not contain any other drug active.

8. The solution of claim 1 which consists of the recited components.

9. The solution of claim 1 specifically as the following formulations:
(a) the phenobarbital sodium is present in an amount of 25 mg/mL;
the C1-C4 alcohol is ethanol and is present in an amount of about 140 mg/mL;
the polypropylene glycol is present in an amount of about 809 mg/mL; and
wherein the solution contains no more than 40 mg/mL water; or
(b) the phenobarbital sodium is present in an amount of 55 mg/mL;
the C1-C4 alcohol is ethanol and is present in an amount of about 140 mg/mL;
the polypropylene glycol is present in an amount of about 779 mg/mL; and
wherein the solution contains no more than 40 mg/mL water; or
(c) the phenobarbital sodium is present in an amount of 90 mg/mL;
the C1-C4 alcohol is ethanol and is present in an amount of about 140 mg/mL;
the polypropylene glycol is present in an amount of about 754 mg/mL; and
wherein the solution contains no more than 40 mg/mL water; or
(d) the phenobarbital sodium is present in an amount of 150 mg/mL; and
the C1-C4 alcohol is ethanol and is present in an amount of about 140 mg/mL;
the polypropylene glycol is present in an amount of about 694 mg/mL; and
wherein the solution contains no more than 40 mg/mL water.

10. A sealed container that includes therein about 0.5 to about 20 mL of the phenobarbital sodium solution of claim 1.

11. The sealed container of claim 10 which is sterilized.

12. The sealed container of claim 10 which is a syringe or vial.

13. The sealed container of claim 10 which has a headspace that has an oxygen content of less than 10% by volume or less than 5% by volume.

14. A method for making the phenobarbital sodium solution according to claim 1 which comprises admixing the phenobarbital sodium with the alcohol and glycol and then adjusting the pH to the desired range as necessary by the addition of the acid or base.

15. The method of claim 14 which further comprises filling a container with about 0.5 to about 20 mL of the solution; and sealing the container.

16. The method of claim 14 which further comprises sterilizing the container and sealing the sterilized container.

17. The method of claim 14 which further comprises providing a headspace in the sealed container that contains oxygen in an amount of less than 10% by volume or less than 5% by volume by adding nitrogen to the container.

* * * * *